United States Patent
Watanabe (10) Patent No.: US 6,442,414 B1
(45) Date of Patent: Aug. 27, 2002

(54) MAGNETIC RESONANCE IMAGING APPARATUS

(75) Inventor: Shigeru Watanabe, Ibaraki-ken (JP)

(73) Assignee: Hitachi Medical Corporation, Chiyoda-ku (JP)

( * ) Notice: Subject to any disclaimer, the term of this patent is extended or adjusted under 35 U.S.C. 154(b) by 0 days.

(21) Appl. No.: 09/623,351

(22) PCT Filed: Mar. 3, 1999

(86) PCT No.: PCT/JP99/01007

§ 371 (c)(1), (2), (4) Date: Sep. 1, 2000

(87) PCT Pub. No.: WO99/44501

PCT Pub. Date: Sep. 10, 1999

(30) Foreign Application Priority Data

Mar. 4, 1998  (JP) .............................................. 10-52341

(51) Int. Cl.$^7$ .............................................. A61B 5/055
(52) U.S. Cl. ........................ 600/419; 600/411; 324/306; 324/307; 324/309
(58) Field of Search ................................ 600/407, 410, 600/411, 419; 324/307, 304, 306

(56) References Cited

U.S. PATENT DOCUMENTS

| | | | | |
|---|---|---|---|---|
| 4,609,872 A | * | 9/1986 | O'Donnell | 324/306 |
| 5,331,279 A | * | 7/1994 | Hatanaka | 324/306 |
| 5,771,893 A | * | 6/1998 | Kassai et al. | 324/306 |
| 6,002,254 A | * | 12/1999 | Kassai et al. | 324/306 |
| 6,043,655 A | * | 3/2000 | Makita et al. | 324/307 |

* cited by examiner

Primary Examiner—Marvin M. Lateef
Assistant Examiner—Runa Shah Qaderi
(74) Attorney, Agent, or Firm—Cooper & Dunham LLP (57) ABSTRACT

An MRI apparatus having an ability of displaying images of flow in different directions in distinguishable manner. When this MRI apparatus performs multi-slice acquisition with a predetermined repetition time TR by selecting a plurality of slices approximately perpendicular to the flow direction of an object to be examined, it performs a first measurement of exciting the plurality of slices in a first order and a second measurement of exciting the same slices in the opposite order to obtain two kinds of data whose signal intensity differs depending on the flow direction. The two kinds of data obtained by two measurements are subjected to subtraction operation to obtain data with different signs depending on the flow direction. These signs combined with the signal intensity are made into images where flow in opposite directions are distinctively depicted. In the multi-slice acquisition, slices are selected so that adjacent slices partially overlap in the direction of the thickness of the slice. Thereby signals of a static part can be suppressed and contrast of flow images after substraction can be enhanced. EPI method of very short imaging time can be employed for the imaging sequence of MRA according to the present invention.

12 Claims, 8 Drawing Sheets

Fig. 7

MAGNETIC RESONANCE IMAGING APPARATUS

FIELD OF THE INVENTION

The present invention relates to a magnetic resonance imaging (abbreviated as "MRI" hereinafter) apparatus for obtaining tomograms of desired sections of an object to be examined by utilizing nuclear magnetic resonance (abbreviated as "NMR" hereinafter). In particular, it relates to an MRI apparatus capable of distinguishing the direction of blood flow when depicting the travel of blood flow.

RELATED ART

One known imaging ability of an MRI apparatus is MR angiography (abbreviated as "MRA" hereinafter), which depicts blood flow without using an imaging contrast agent or the like. Typical imaging methods of blood flow using the MRI apparatus include the time-of-flight (TOF) method, which utilizes the inflow effect of blood into slice planes, and the phase method, which utilizes phase dispersion of flow spins caused by gradient magnetic field in the direction of the flow. The phase method includes the phase-sensitive (PS) method and the phase-contrast (PC) method. The PS method depicts blood flow by subtraction of data acquired in a sequence compensating the phase dispersion of flow (rephase sequence) and data acquired in a sequence promoting the phase dispersion to diminish flow signals (dephase sequence). The PC method utilizes a pair of gradient magnetic field pulses (flow encoding pulses) imparting different phase rotation to flow spins, and depicts the blood flow by applying these pulses to obtain a pair of data and performing complex subtraction of these flow-encoded data.

Each of these conventional flow imaging methods has merits and demerits and is employed in accordance with the purpose of imaging. For example, the 2D-TOF method, which performs RF irradiation onto an object region with a short repetition time TR (presaturation), should use a short-TR sequence such as the gradient echo method as its imaging sequence and cannot employ a fast sequence such as EPI. In addition, since signals of flow spins flowing into the region from any direction are enhanced, arterial flow and venous flow cannot be distinguished. A technique of pre-saturating a region adjacent to the imaging region maybe employed but, in this case, only one of the arterial flow and venous flow can be visualized.

On the other hand, the PC method also provides a technique for distinguishing one of the arterial flow and venous flow from the other by taking subtraction between flow-encoded phase images with different polarities. However, when the flow velocity is high enough to cause a phase shift of more than $\pi$, the PC method produces a problematic aliasing artifact. In addition, since the sequence of the PC method is not of the flow-rephase type, it cannot cope with turbulent flow or variance of the flow velocity, and blackened flow images or artifacts are therefore likely to occur. Moreover, a two-dimension PC method aiming at quantitative measurement of flow velocity cannot thicken the thickness of a slice including blood vessels and is not suitable for observing the overall travel of blood together with quantitative measurement.

Therefore, an object of the present invention is to provide an MRI apparatus having a new ability of blood flow imaging with little artifact and capable of distinguishing the arterial and venous flows (depicting blood flow direction) together with enabling observation of all vessels.

Another object of the present invention is to provide an MRI apparatus capable of employing a fast imaging sequence such as EPI and thereby imaging flow in a short measuring time.

SUMMARY OF INVENTION

In order to achieve the above object, the present invention provides an MRI apparatus having a function of, for a plurality of slices, performing excitation of a slice by application of radio frequency magnetic field and measurement of echo signals successively, and reconstructing blood images using the obtained echo signals, wherein the apparatus performs, during performing said function, a first measurement of exciting the plurality of slices in a first order and a second measurement of exciting the slices in an order opposite to the first order to obtain two kinds of data for each slice, and subtraction operation between the two kinds of data for each slice to obtain signals from blood flows in different directions as data having different signs.

Specifically, the MRI apparatus of the present invention comprises means for generating a static magnetic field in a space where an object to be examined is accommodated, means for generating gradient magnetic fields to impart a gradient to the static magnetic field, a transmitting system for repeatedly applying radio frequency pulses according to a predetermined pulse sequence to cause nuclear magnetic resonance of nuclear spins of atoms constituting living tissue of the object, a receiving system for detecting echo signals emitted by the nuclear magnetic resonance, a signal processing system for performing image reconstruction operation using the echo signals detected by the receiving system, means for displaying the obtained images, and a controlling system for controlling operations of the gradient magnetic field generating means, transmitting system, receiving system, and signal processing system, wherein the controlling system performs a first measurement of repeatedly exciting the plurality of slices in a first order with a predetermined repetition time and a second measurement of exciting the plurality of slices in an order opposite to the first order with the same repetition time to obtain two kinds of data for each slice, and the signal processing system performs subtraction operation between the two kinds of data for each slice to obtain signals from blood flows in opposite directions as data with different signs.

The magnetic resonance angiography (MRA) method of the present invention is a method of, for a plurality slices, performing excitation of a slice by application of radio frequency magnetic field and measurement of echo signals successively, and reconstructing a blood image using the obtained echo signals, which comprises the steps of (a) performing a first measurement of exciting the plurality of slices in a first order and a second measurement of exciting the slices in an order opposite to the first order to obtain two kinds of data for each slice, and (b) performing subtraction operation between the two kinds of data for each slice to obtain signals from blood flows in different directions as data having different signs.

In the first measurement, where the plurality of slices are excited successively in the first direction (direction A), blood flow in the direction A is repeatedly excited with a relatively short repetition time and signals from the blood flow spins become relatively weak. On the other hand, the repetition time TR of blood flow excitation in the opposite direction (direction B) becomes relatively long and signals thereof become approximately the same as that of static spins. In the second measurement, where the same plural slices are excited successively in the direction B opposite to the first direction, signals from the blood flow in the direction B become relatively weak and signals from the blood flow in the direction A become relatively strong, contrary to the first measurement. Accordingly, when subtraction is performed between data obtained by these two kinds of measurements, the pixel value (signal intensity) of the static part becomes 0 and, for flow spins, the sign of the data differs depending on the flow direction.

The MRA of the present invention preferably further includes step (c) of saturating at least one of region adjacent to the object region by applying a radio frequency magnetic field prior to the step (a) (pre-saturating step).

In the slice positioned at each side of the object region, signals of blood spins flowing into the slice would not be suppressed by multiple excitations and would not be distinguished from those from blood spins flowing out of the slice. However, by pre-saturating the region adjacent to the object region, signals are suppressed by multiple excitations and, therefore, blood spins of different directions, i.e., inflow spins and outflow spins, become distinctive. Thus, ability of imaging blood flow can be improved throughout the object region. Instead of pre-saturating the region adjacent to the object region, data of slices at both sides may be deleted from data to be processed in step (b). This deletion of data should be construed as being within the scope of the present invention.

In the MRA of the present invention, it is also preferred that, in the measurement of each slice, the slice be selected so that it partially overlaps each adjacent slice.

When each slice is excited so that the adjacent slices overlap each other, a static part of the overlapped portion is repeatedly excited and, therefore, signal intensity of the static part can be more suppressed than when slices do not overlap. Thereby, the blood flow imaging ability can be improved.

Gradient echo type sequence maybe employed as the imaging sequence of the present invention and the number of echo signals measured at each excitation maybe one or more. Since blood signals can be depicted with high contrast relative to that of the static part even though the same slice is not excited many times, a multiple-echo sequence (including EPI), which measures a plurality of echo signals everyone excitation, maybe employed.

BRIEF DESCRIPTION OF DRAWINGS

FIGS. 2(a) and (b) show exemplary imaging sequences performed by a sequencer.

BEST MODE FOR CARRYING OUT OF THE INVENTION

The present invention will now be explained in detail with reference to the specific examples shown in the appended drawings.

Figure 8:
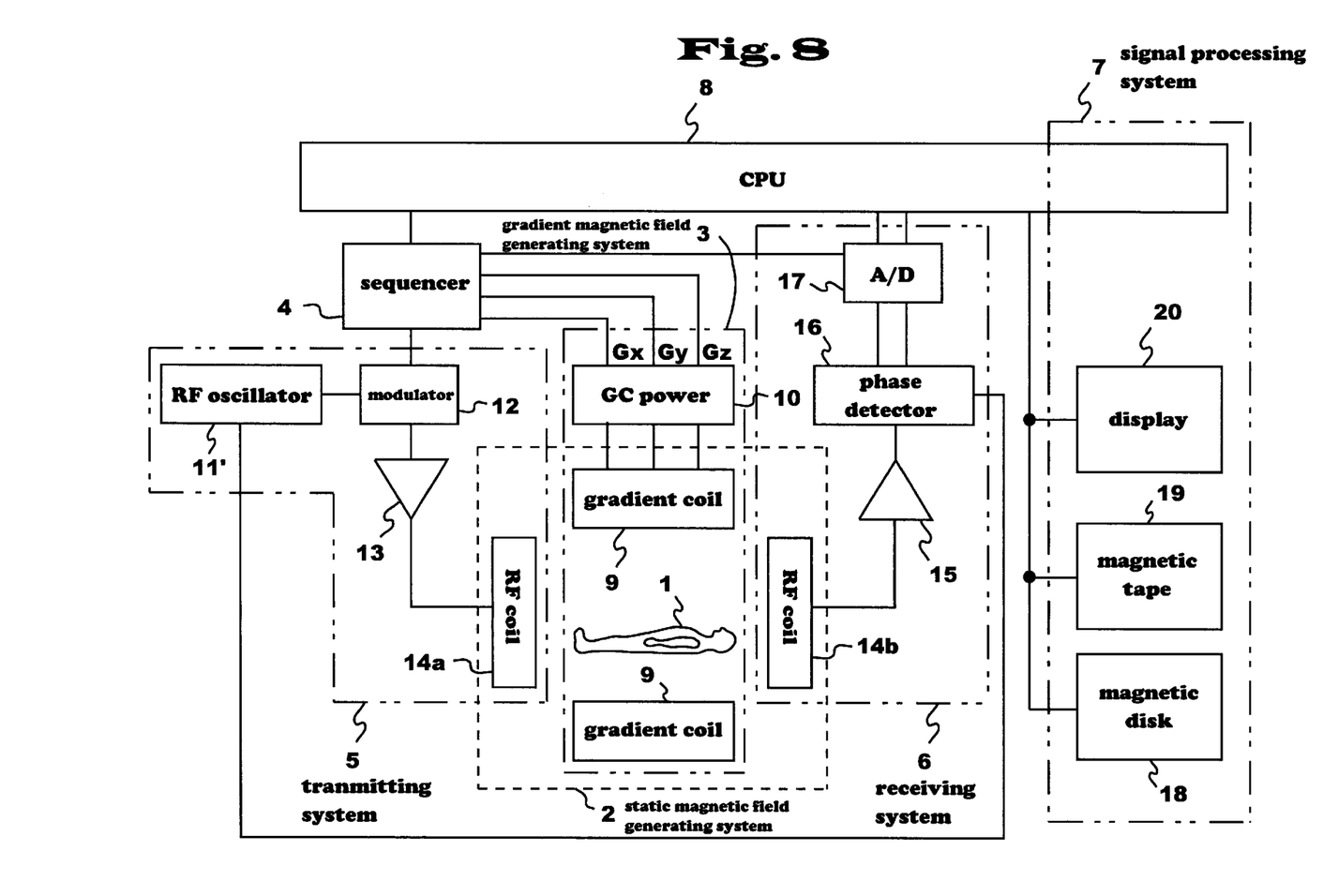
FIG. 8 is an overall block diagram representing a system of the MRI apparatus of the present invention.

FIG. 8 is an overall block diagram showing the system of an MRI apparatus that can be used according to the present invention. This MRI apparatus is for obtaining tomograms of an object to be examined by utilizing NMR phenomenon, and comprises a static magnetic field generating magnet 2, a gradient magnetic field generating system 3, a transmitting system 5, a receiving system 6, a signal processing system 7, a sequencer 4 and a central processing unit (CPU) 8, as shown in FIG. 8.

The static magnetic field generating magnet 2 generates a uniform static magnetic field around an object to be examined 1 in a direction parallel or perpendicular to the body axis of the object 1 and comprises a magnet for generating static magnetic field in a space around the object 1 such as a permanent magnet, a resistive magnet or a superconductive magnet.

The gradient magnetic field generating system 3 consists of gradient magnetic field coils 9 wound in the directions of three axes, X, Y, and Z, and a gradient magnetic field power supply 10 for driving the gradient magnetic field coils. The gradient magnetic field power supply 10 is driven according to instructions from a sequencer 4 (explained later) and applies gradient magnetic fields Gx, Gy, and Gz in the direction of the three axes, X, Y, and Z, to the object. A slice plane of the object 1 is determined by selecting the amplitudes of these gradient magnetic fields.

The sequencer 4, is for repeatedly applying RF pulses in a given pulse sequence to cause nuclear magnetic resonance of nuclei of atoms constituting the living tissues of the object 1. The sequencer 4 operates under the control of the CPU 8, and sends various kinds of instructions necessary for collecting data for obtaining tomograms of the object 1 to the transmitting system 5, the gradient magnetic field generating system 3 and the receiving system 6.

The transmitting system 5 is for an producing RF magnetic field in order to cause nuclear magnetic resonance of nuclei of atoms constituting the living tissues of the object 1 in accordance with the RF pulse transmitted from the sequencer 4, and consists of an RF oscillator 11, a modulator 12, an RF amplifier 13 and an RF coil for transmission 14a. The transmitting system 5 amplitude-modulates the radio frequency pulses output from the RF oscillator 11 by the modulator 12 in accordance with instructions from the sequence 4. The amplitude-modulated RF pulses are amplified by the RF amplifier 13 and supplied to the RF coil 14a located in the vicinity of the object 1 so that electromagnetic waves are radiated onto the object 1.

The receiving system 6 is for detecting echo signals (NMR signals) elicited through nuclear magnetic resonance of atomic nuclei of the living tissues of the object 1, and consists of an RF coil 14b for receiving electromagnetic waves, an amplifier 15, a quadrature phase detector 16 and an A/D converter 17. Electromagnetic waves (NMR signals) emitted from the object 1 in response to the electromagnetic waves radiated from the RF coil 14a for transmission are detected by the RF coil 14b located in the vicinity of the object 1, input into the A/D converter 17 through the amplifier 15 and the quadrature phase detector 16 and thereby converted into digital signals. The sampling data obtained by the quadrature phase detector 16 at times instructed by the sequencer 4 are corrected as two series data and transferred to the signal processing system 7.

The signal processing system 7 consists of the CPU 8, a recording medium such as a magnetic disk 18 and magnetic tape 19, and a display unit 20 such as a CRT. The CPU 8 performs processing such as Fourier transform, calculation of correction coefficient and image reconstruction, thereby imaging a signal intensity distribution or distribution obtained by subjecting a plurality of signals to suitable arithmetic operations on a certain section and displaying them as a tomogram on the display unit 20.

In FIG. 8, the transmission and receiving RF coils 14a and 14b and the gradient magnetic field coils 9 are disposed within the magnetic field formed by the static magnetic field generating magnet 2 enclosing the space around the object to be examined 1.

An imaging sequence for flow imaging performed by the sequencer 4 of the thus constituted MRI apparatus will now be explained.

Figure 1:
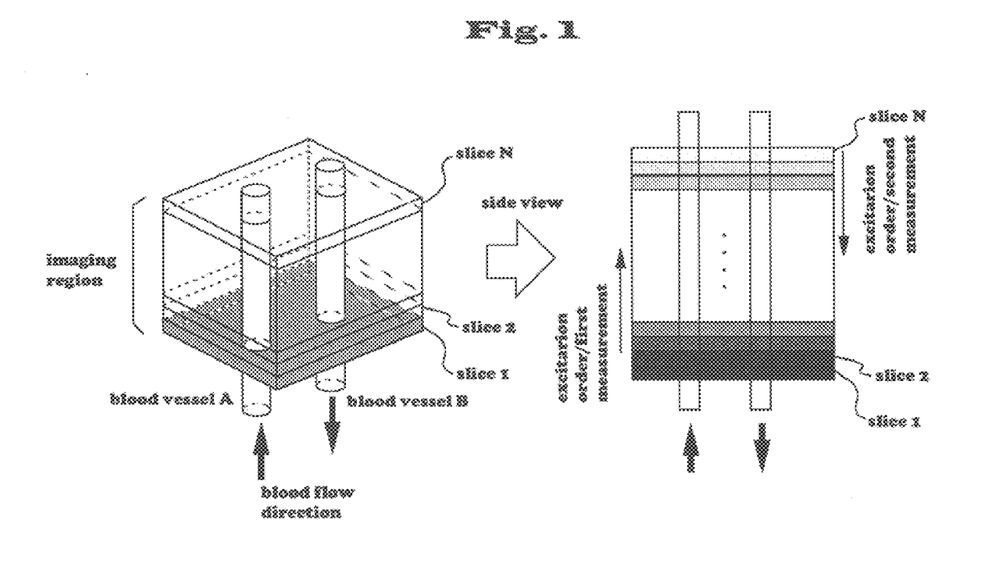
FIG. 1 is an explanatory view of MRA measurement performed by an MRI apparatus that is an embodiment of the present invention.

FIG. 1 shows a simplified model of a region to be examined by the MRI apparatus of the present invention. In the present invention, an object region including blood vessels A and B is divided into slices so that the slice plane is approximately perpendicular to the blood vessels and these slices are measured by multi-slice acquisition in two different orderings.

Figure 2:
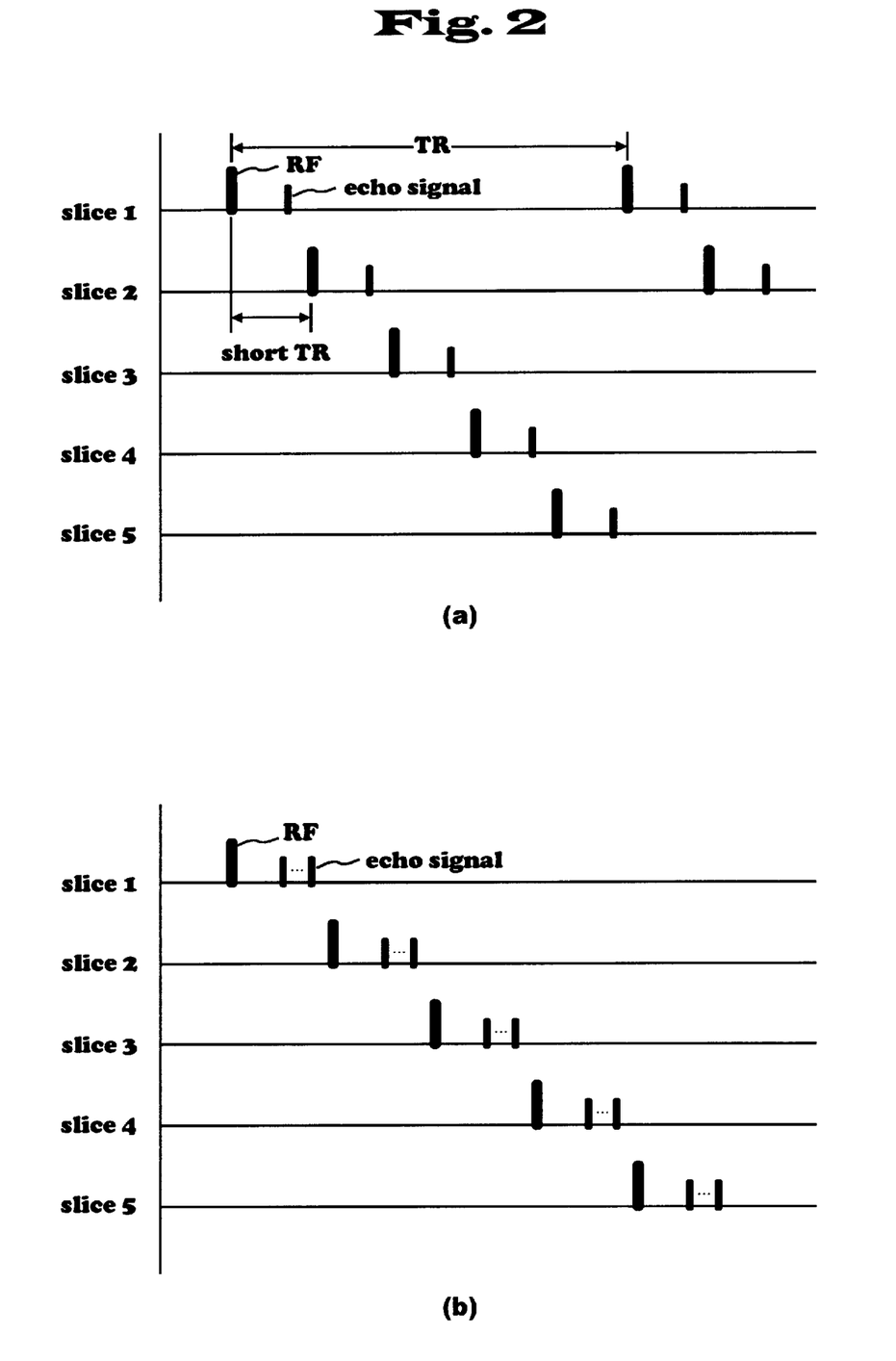

The multi-slice acquisition includes, as shown in FIG. 2(a), excitation of a slice by an RF pulse and collection of echo signals successively for each slice within a repetition time TR for one slice, and this step is repeated while changing the phase encode. Although only one and a half repetition steps are shown in FIG. 2(a), the imaging sequence is repeatedly conducted until echo signals of a phase encode number necessary for image reconstruction are collected.

Although the figure does not show the imaging sequence specifically, it may be an imaging sequence according to the gradient echo method (FIG. 2(a)), where one echo signal is generated by reversing a gradient magnetic field after one selective excitation of a slice by RF pulse irradiation, or a single-shot or multi-shot EPI sequence (FIG. 2(b)), where a plurality signals (only two signals are shown in the figure for simplification) are collected by reversing the polarity of a gradient magnetic field several times while applying phase-encoding gradient magnetic field pulses after one selective excitation of a slice by RF pulse irradiation. In the multi-shot EPI sequence, the sequence shown in FIG. 2(b) is repeated while changing the phase encode offset. For simplification, only slices 1 to 5 are shown in the figure but several tens of slices may be measured within the TR.

In the first measurement, this multi-slice acquisition, i.e., excitation/acquisition, is conducted successively from the lowest slice 1 to the uppermost slice N in FIG. 1, for example from the leg side to the head side of a human body. In the second measurement, the excitation/acquisition is conducted successively from the uppermost slice N to the lowest slice 1.

In case that the slices are excited in the order of the first measurement, flow within the blood vessel A in the direction of excitation order is subjected to multiple excitations at a significantly smaller interval than the repetition time TR as moving from slice 1 to slice 2, and to slice 3. This causes depression of signal intensity of flow A. On the other hand, flow within the blood vessel B in the opposite direction to the excitation order is excited at an interval approximately the same as the repetition time TR of a static part, which is longer than the TR of flow A. Accordingly, signal intensity of flow B becomes larger.

In the second measurement, since the order of slice excitation is opposite to that of the first measurement, the intensity of signals of flow A becomes higher and that of signals of flow B becomes lower.

The present invention utilizes this difference between the signal intensities of flow A and flow B, i.e., that the intensities are opposite in these two different measurements, to enables depiction of the flows in the different directions.

Figure 3:
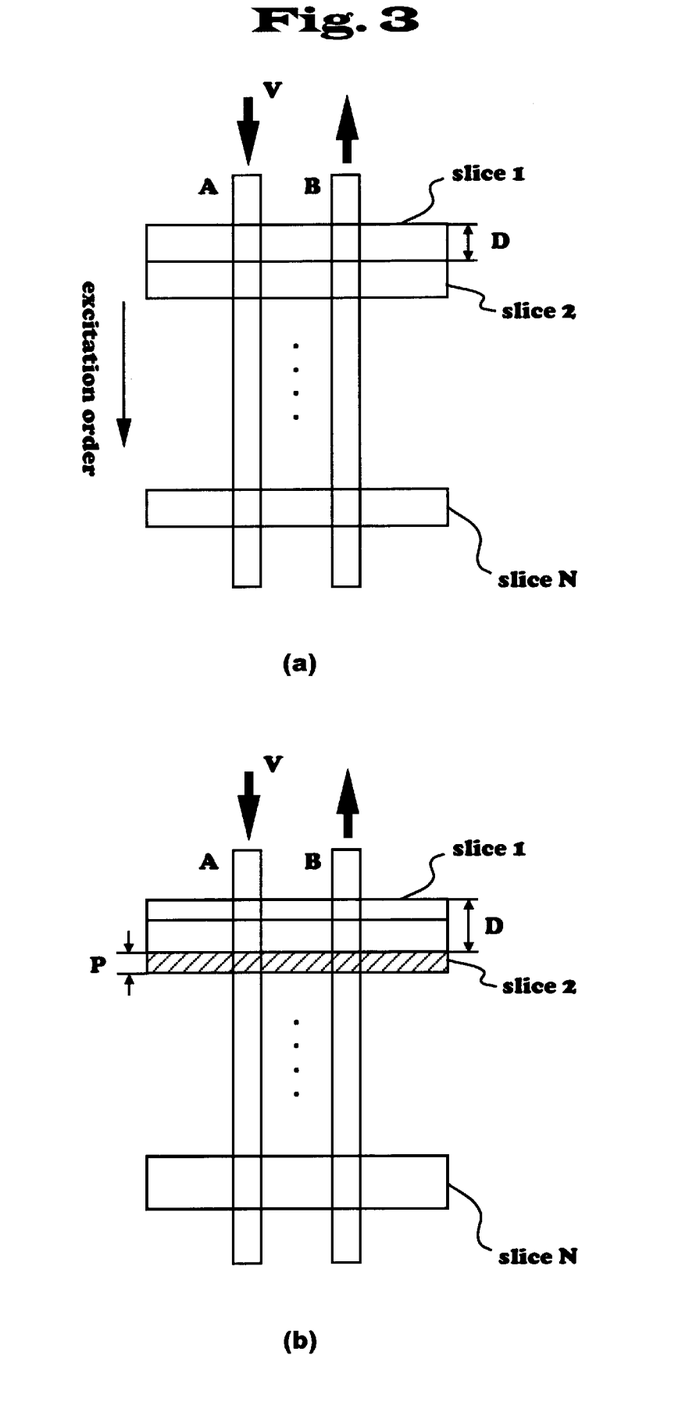
FIG. 3 is an explanatory view of the principle of MRA measurement according to the present invention.

This will be further explained with reference to FIG. 3.

First, a case where there is no overlap between slices is considered (FIG. 3(a)). The blood flow A excited in the slice 1 moves into the slice 2. The time until the blood flow is excited again (effective repetition time, eTR) may differ depending on the blood flow velocity v, and is represented as follows.

When the blood flow velocity v is relatively high and satisfies the following condition: $v \geq 2D/(TR/N)$, where D represents slice thickness, TR represents a predetermined repetition time and N represents the number of slices excited within TR (the same hereinafter), at the time when the slice 2 is excited after the excitation of the slice 1, the blood flow A has already moved to the slice 3 or another following slice. Therefore, the effective TR (eTR) becomes infinite (eTR=∞). Accordingly, there is no depression of the signal intensity due to multiple excitations.

When the blood flow velocity v satisfies the following condition: $D/(TR/N) \leq v < 2D/(TR/N)$, a part or all of the blood flow excited within the slice 1 should be present in the slice 2 at the time when the slice 2 is excited. Therefore, in this case, the effective repetition time eTR is equal to TR/N (eTR=TR/N) as for the blood flow present in the slice 2, and it is infinite (eTR=∞) as for the blood flow moved to the slice 3 or another following slice. The signal ratios of blood flow spins corresponding to these different eTRs differ depending on the blood flow velocity v, and the ratio of the signal of blood flow spin obtained with eTR equal to TR/N increases as v becomes smaller.

When the flow velocity satisfies $v=D/(TR/N)$, eTR becomes shortest, i.e., TR/N, for the whole blood flow. The signal intensity as a whole is obtained by adding signal intensities, including phases thereof, each corresponding to eTR of each blood flow spin and multiplied by the existing ratios thereof.

When the flow velocity is low, i.e., when it satisfies $v<D/(TR/N)$, eTR is equal to TR/N (eTR=TR/N) as for a blood stream flowing into the slice 2, and eTR of a blood flow remaining in the slice 1 is approximately equal to the predetermined eTR. Also in this case, the signal intensity is a weighted mean of the signals of these blood flow spins with different eTRs according to the ratios thereof.

As described above, in the blood flow A, the signal is depressed proportionally to the ratio of blood flow where eTR is TR/N, except for the case where $v \geq 2D/(TR/N)$.

As for the blood flow B, which flows in the opposite direction, blood which has not been excited flows into the slice 2 from the slice 3, and its eTR is therefore infinite. Therefore, there is no decline of signal intensity. Since a static part of each slice is not excited during excitation of the slice directly before it, the effective repetition time eTR becomes almost the same as the predetermined TR.

Thus, when there is no overlap between slices, only the blood flow A undergoes multiple excitations depending on blood flow velocity v. Therefore, only the signal of the blood flow A can be effectively controlled by selecting the thickness D of slices and the number N of slices taking account of the blood flow velocity.

Next, a case where contiguous slices are sequentially excited with a predetermined interval P (amount of overlap= D−P) as shown in FIG. 3(b) is considered. In this case, when the blood flow velocity satisfies the following condition: $v \geq (D+P)/(TR/N)$, the blood flow A has already moved to the following slice 3 or another following slice during the time from excitation of the slice 1 to that of the slice 2. Therefore, the effective TR (eTR) becomes infinite (eTR=∞). Thus, there is no depression of the signal intensity due to multiple excitations.

When the blood flow velocity v satisfies the following condition: $P/(TR/N) \leq v < (D+P)/(TR/N)$, a part or all of the blood flow excited within the slice 1 is present in the slice 2 at the time when the slice 2 is excited. Therefore, the blood flow present in the slice 2 comes to have an effective repetition time eTR equal to TR/N (eTR=TR/N), and to thus subjected to multiple excitations. The other portion has already moved to the slice 3 or another following slice, and thus its eTR is infinite (eTR=∞) Also in this case, the ratio of the blood flow having undergone multiple excitations differs depending on the blood flow velocity v, and the signal intensity is obtained by adding signal intensities multiplied by the ratios thereof.

When the blood flow velocity is extremely low, and satisfies the condition: $v < P/(TR/N)$, eTR can be considered to be substantially the same as that of a static part. Therefore, when there is overlap between slices, at least a part of the blood flow A also undergoes multiple excitations depending on its velocity, except for a case where the velocity is extremely high, and signal intensity is depressed proportional to the ratios.

As for the blood flow B, which flows in the opposite direction, when the flow velocity satisfies the condition $v \geq (D-P)/(TR/N)$, the effective repetition time eTR is infinite (eTR=∞). On the other hand, when it satisfies the condition: $v < (D-P)/(TR/N)$, the blood flow undergoes different excitation depending on whether it is in an overlap part and whether the slice is a slice present upstream in the blood flow. That is, when a blood flow is excited in a slice and moved in a direction opposite to the excitation direction, the part remaining in the overlap part will be excited by subsequent excitation. Therefore, its effective repetition time eTR satisfies the condition: TR/N<eTR<TR. On the other hand, as for a non-overlapping part, a blood flow which has been excited during the repetition time of the previous phase encoding step for exciting an upstream slice may flow therein. In such a case, the effective repetition time eTR is equal to nTR/N(eTR=nTR/N) where n is an integer determined by TR, N, v and P, and n is smaller than N. However, in an upstream slice, since no blood flow excited in the previous phase encoding step flows into it, eTR becomes infinite (eTR=∞). The signal intensity of the blood flow B becomes a weighted mean of the signals of the blood flow spins with these three kinds of effective repetition times eTR. Since all of these eTRs are longer than TR/N, signal suppression by multiple excitations as in the blood flow A does not occur.

As for a static part, a part where the slice 1 and the slice 2 do not overlap each other (hatched part in the figure) has not been excited during the excitation of the previous slice. Therefore, its effective repetition time eTR is substantially the same as the predetermined TR. On the other hand, the eTR of the overlap part becomes TR/N (eTR=TR/N), and that part undergoes multiple excitations. Therefore, the signal intensity of a static part can be controlled by suitably selecting the amount of overlap. Therefore, it is possible to obtain different signal intensities of the blood flow A, static part and the blood flow B, which decrease in this order, and thereby the contrast of the angiography after the subtraction operation can be enhanced, which will be explained hereinafter. If the amount of overlap is too large, the number of slices for covering the whole object region will be large. This eventually leads to prolonged measuring time and saturation of slow blood flow. Therefore, the amount of overlap is selected to be about 20–80% of the slice thickness, preferably 50% or less of the slice thickness. However, the amount of overlap maybe increased for arterial vessels and the like.

As explained above, in both cases shown in FIGS. 3(a) and 3(b), different signal intensities can be obtained depending on the direction of the blood flow. Further, if a reversed excitation order is used for the measurement, the difference in signal intensity maybe imparted in an exactly inverted manner.

Now, means for image reconstitution from data obtained from two times of measurements wherein the signal intensities are imparted indifferent manners depending on the flow direction will be explained.

Figure 4:
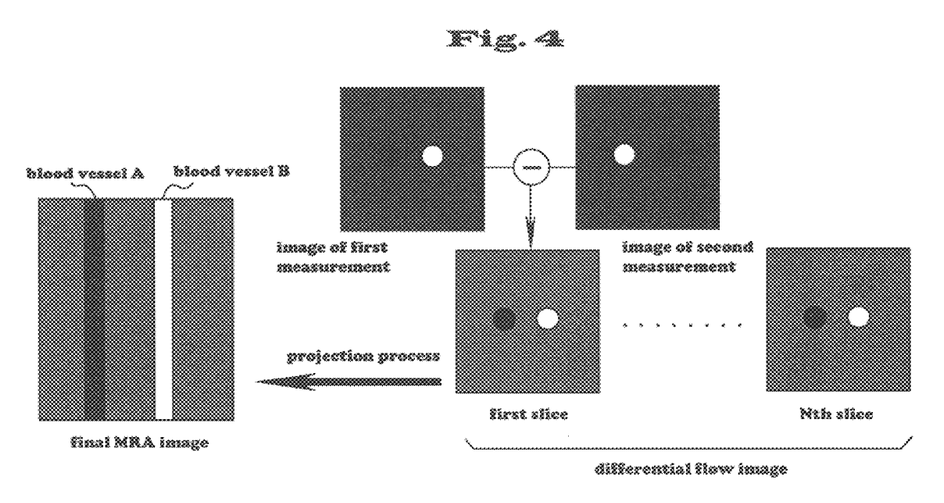
FIG. 4 shows exemplary image processing in the MRI apparatus of the present invention.

The aforementioned two kinds of multi-slice acquisitions provide a pair of image data sets for each slice as shown in FIG. 4. In one set of images obtained for one and the same slice, the blood vessel A is depicted with weak signal intensity and the blood vessel B is depicted with strong signal intensity in one group of data (image obtained by the first measurement), and the blood vessel B is depicted with weak signal intensity and the blood vessel A is depicted with strong signal intensity in the other group of data (image obtained by the second measurement).

Then, a subtraction is performed between the data in one pair of data sets (for example, the image data set obtained from the second measurement is subtracted from the image data set obtained by the first measurement). The subtraction may be performed with complex data or absolute values after each data set is reconstituted as an image, or the reconstitution may be performed after the subtraction of complex data using signal data before the reconstitution. This operation causes a signal loss of static parts and provides an image containing only blood vessels. In this image, pixel values have different signs depending on the direction of the blood flow. The aforementioned subtraction is performed for each slice, and thus there are obtained subtraction images in a number of the slices.

Then, the obtained subtraction images are subjected to projection operation to form a projected blood vessel image of the whole object region. Known methods for obtaining a projected image from multiple two-dimensional images of contiguous slices each containing a part of a vessel includes the maximum intensity projection method (MIP) and the minimum intensity projection method (MinIP) using a ray tracing technique. In the present invention, blood vessels for both directions of blood flow are depicted using the maximum intensity projection method and the minimum intensity projection method in combination.

Figure 5:
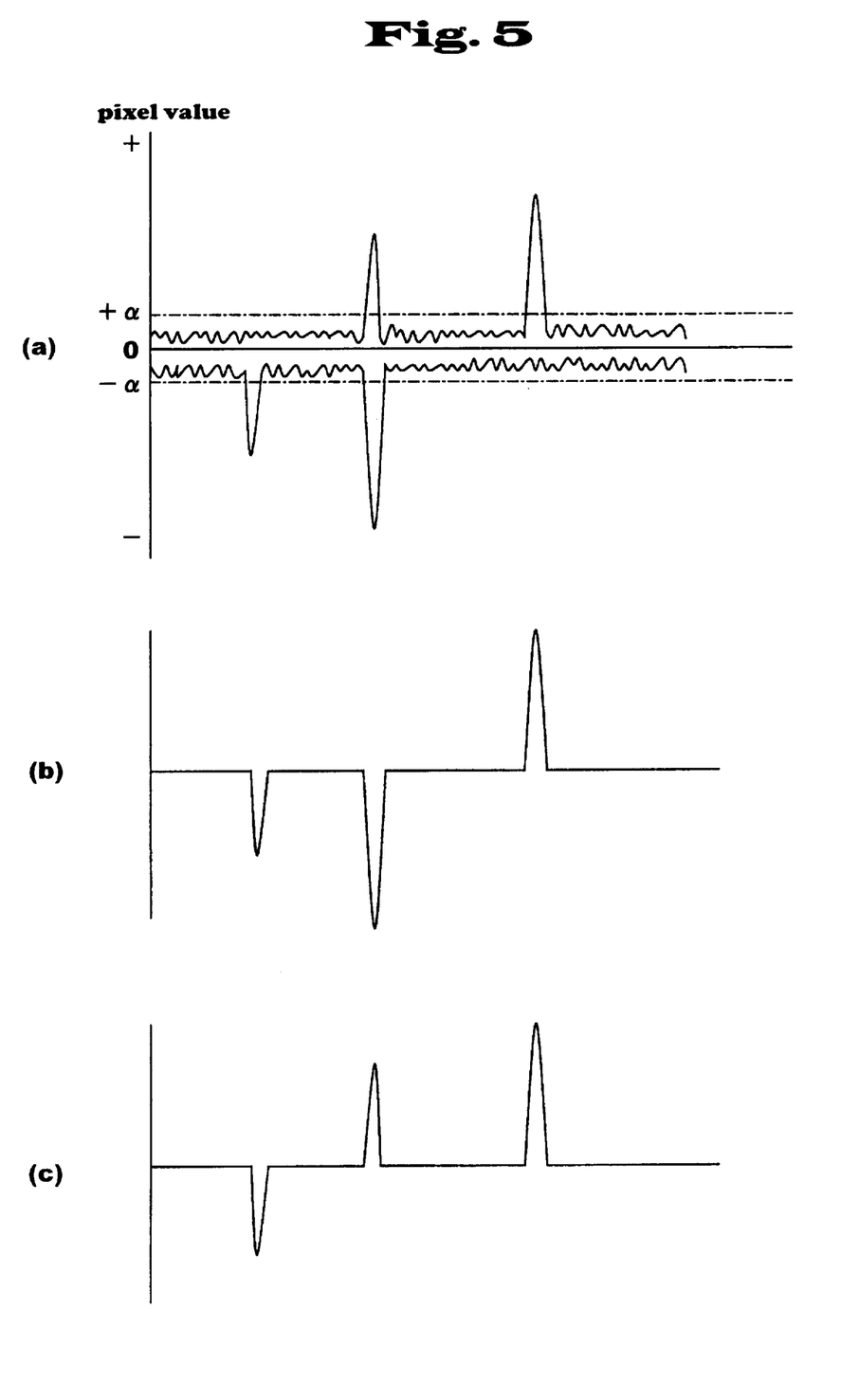
FIG. 5 is an explanatory view of a projection process in the MRI apparatus of the present invention.

As explained above, the subtraction images contain data of different signs. Therefore, if only the MIP treatment or only the MinIP treatment is performed, only blood vessels for one blood flow direction are depicted. To avoid this, the following operation is performed. First, as shown in FIG. 5(a), a threshold value α is determined for both positive and negative signal intensities. A signal having an absolute value not greater than the threshold value α is considered to be that of a tissue other than a blood vessel, and is displayed in gray color as a zero level or α. A signal having an absolute value exceeding the threshold value α is considered to be that of a blood vessel. If the value is positive, it is displayed in white, and if negative, it is displayed in black, for example.

This makes it possible to display the blood vessel A and the blood vessel B, in which the blood flows in opposite directions, respectively in black and white on a gray background, for example.

As for a case where a positive signal and a negative signal are overlapped on an optical axis, the one having larger absolute value between the positive and negative signals may be displayed (FIG. 5(b)). Alternatively, one or the other of the positive and negative signals can be assigned priority beforehand and that one displayed according to the determined rule (FIG. 5(c)). The method to be employed can be decided in consideration of the requirements of the diagnosis. The method of FIG. 5(b) is suitable for preferentially imaging blood vessels with higher signal values, and the method of FIG. 5(c) is suitable for preferentially imaging either of arteries or veins.

Figure 6:
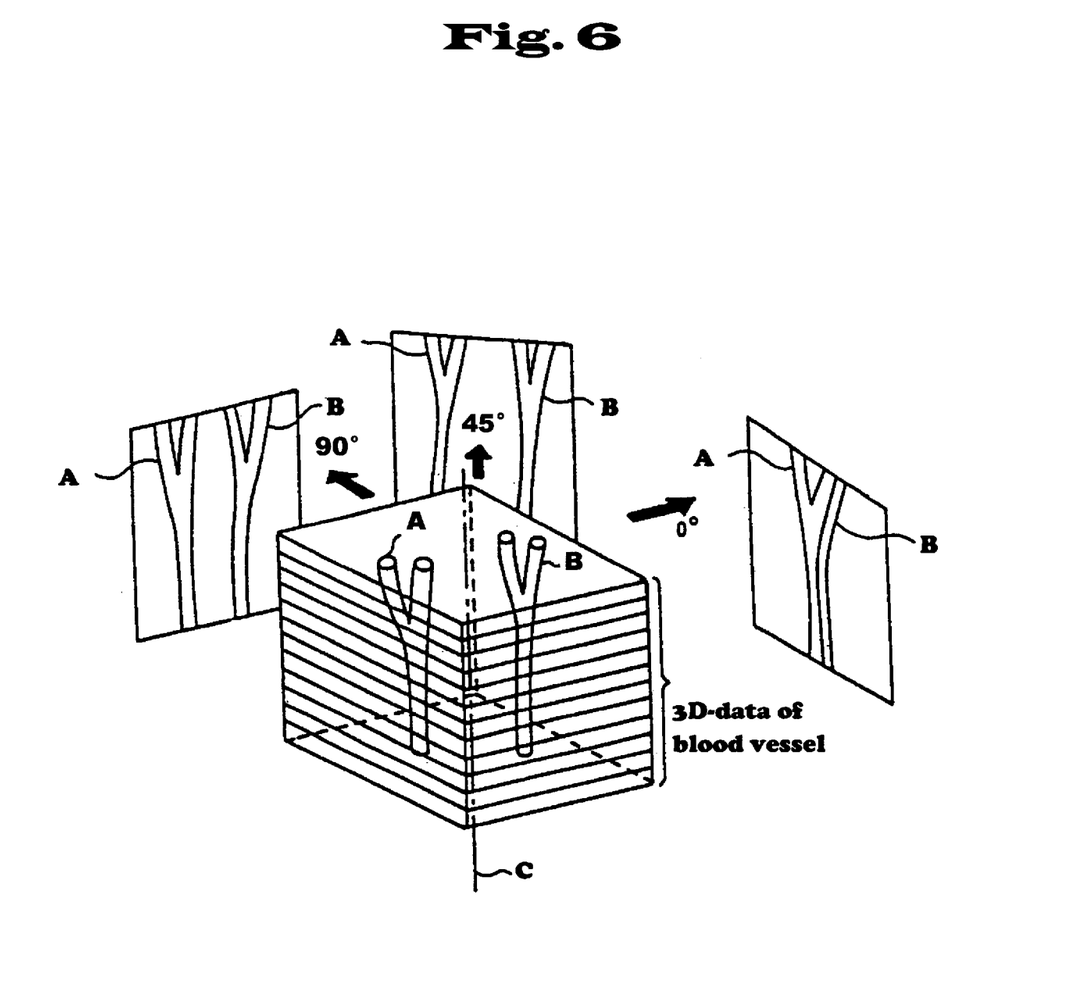
FIG. 6 shows exemplary image processing in the MRI apparatus of the present invention.

The blood flow direction may also be displayed indifferent colors depending on signs, instead of by the monotonous display explained above. That is, they may be made distinguishable by display in different colors, for example, red for positive values and blue for negative values. Further, as in conventional projection operations, the projection direction of the aforementioned projection operation may be arbitrarily decided as, for example, coronary section, sagittal section, transverse section and so forth. Furthermore, as shown in FIG. 6, the image may be rotated around a certain axis C, and projected images are formed every 5–10 degrees from a projector with an angle of about ±45 degrees. They can be displayed as moving images. This makes it possible to recognize structures of blood vessels including three-dimensional relationship and depth of blood vessels, and it becomes possible to observe vessels that are hidden due to the use of the method of FIGS. 5(b) or (c) from a different direction.

As explained above, the MRI apparatus of the present invention utilizes the signal intensity depression due to multiple excitations of blood flowing in the same direction as the excitation direction during multi-slice acquisition, and obtains blood flow signals as data with different signs depending on the blood flow direction by subtraction of data obtained from two kinds of measurements with different excitation directions. In this case, regarding the slice 1 in FIG. 1, the first to be excited, blood flowing into this slice along the direction of excitation does not undergo multiple excitations, and therefore its signal intensity is not lowered. Similarly, regarding the slice N, the first to be excited in the second measurement, signal intensity of blood flowing into this slice along the direction of the excitation is not lowered. Therefore, when subtraction is performed between two sets of data from two measurements with different excitation orders, difference of the blood flow direction becomes ambiguous for the first and last slices, i.e., the slices 1 and N.

In order to eliminate the ambiguous part at the opposite ends of the object region, data of the first and last slices may be deleted. However, it is more preferred for a region adjacent to the slice to be excited first to be preliminarily saturated (presaturated) by RF irradiation.

Figure 7:
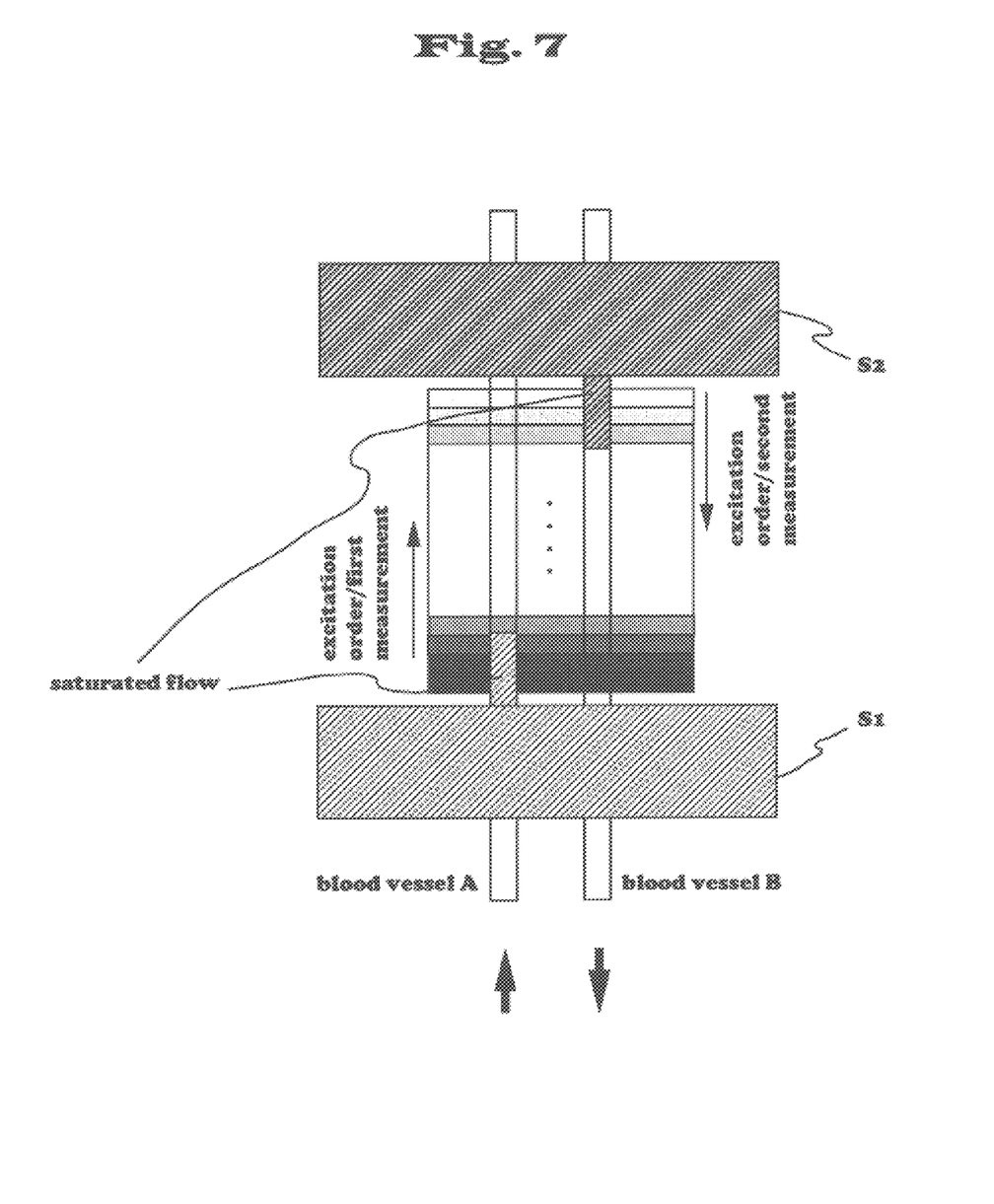
FIG. 7 shows an MRA measurement performed by the MRI apparatus according to another embodiment of the present invention.

An exemplary imaging sequence including this presaturation is shown in FIG. 7. In this embodiment, similarly to the embodiment shown in FIG. 1, the object region is divided into multiple slices approximately perpendicular to the objective blood vessels A and B and multi-slice acquisition is performed, in which first and second measurements are performed with different excitation order of slices. In this embodiment, however, during the multi-slice acquisition of the first measurement, a region S1 (lower region in the figure) adjacent to the slice 1 to be excited first is subjected to RF irradiation to saturate spins in this region. After the first measurement is completed, a region S2 (upper region in the figure) adjacent to the slice n to be excited first is also presaturated to saturate spins when starting the second measurement.

When the slice 1 (or slice N) is excited after the adjacent region is presatuated, since saturated blood flow spins flow into this slice from the saturated region S1 (or region S2), the signals from the blood flow can be lowered. This produces a distinct difference among the signals of the blood vessel A, the static part and the blood vessel B, and hence makes it possible to enhance the ability to ascertain blood flows.

Such presaturation can be performed irrespective of the nature of the imaging sequence, and a presaturation step for the region S1 or S2 may be inserted as a step preceding the multi-slice sequences shown in FIGS. 2(a) and (b).

Further, although the above explanation was made for the cases where the gradient echo method or EPI method is used for the multi-slice sequence of the present invention, the present invention can also be applied in case where the multi-slice sequence utilizes other methods.

As explained above, the MRI apparatus of the present invention makes it possible to depict blood flows of different directions by performing two kinds of multi-slice acquisitions with reversed slice excitation orders as its flow imaging functions and by performing subtraction of data obtained through the multi-slice acquisitions. Further, it can employ EPI for multi-slice acquisitions, in which echoes of a total phase encode number required for image reconstitution can be obtained at one excitation of slices. This makes it possible to obtain an angiogram in an extremely short period of time, i.e., 10 seconds or less.

Furthermore, in the MRI apparatus of the present invention, the measurement is unlikely to suffer from the influence of turbulent flow, which poses a problem in the conventional PC method, and this makes it possible to clearly distinguish blood flow directions even for overlapped arteries and veins.

What is claimed is:

1. A magnetic resonance imaging apparatus comprising:
   means for generating a static magnetic field in a space where an object to be examined is accommodated, means for generating gradient magnetic fields to impart a gradient to the static magnetic field, a transmitting system for repeatedly applying radio frequency pulses according to a predetermined pulse sequence to cause nuclear magnetic resonance of nuclear spins of atoms constituting living tissue of the object, a receiving systems for detecting echo signals emitted by the nuclear magnetic resonance, a signal processing system for performing image reconstruction operation using the echo signals detected by the receiving system, means for displaying the obtained images, and a controlling system for controlling operations of the gradient magnetic field generating means, transmitting system, receiving system, and signal processing system,
   wherein the controlling system performs a first measurement of repeatedly exciting the plurality of slices in a first order with a predetermined repetition time and a second measurement of exciting the plurality of slices in an order opposite to the first order with the same repetition time to obtain two kinds of data for each slice, and the signal processing system performs subtraction operation between the two kinds of data for each slice to obtain signals from blood flows in opposite directions as data with different signs.

2. A magnetic resonance imaging apparatus comprising:
means for generating a static magnetic field in a space where an object to be examined is accommodated, means for generating gradient magnetic fields to impart a gradient to the static magnetic field, a transmitting system for repeatedly applying radio frequency pulses according to a predetermined pulse sequence to cause nuclear magnetic resonance of nuclear spins of atoms constituting living tissue of the object, a receiving systems for detecting echo signals emitted by the nuclear magnetic resonance, a signal processing system for performing image reconstruction operation using the echo signals detected by the receiving system, means for displaying the obtained images, and a controlling system for controlling operations of the gradient magnetic field generating means, transmitting system, receiving system, and signal processing system, wherein the controlling system performs imaging of a predetermined region by a plurality of slice acquisitions, and effects control so that a plurality of slices are excited in order to obtain echo signals and the same are excited in an opposite order to obtain echo signals, the obtained echo signals are subtracted for corresponding slices, and the subtracted data are reconstructed.

3. A magnetic resonance imaging apparatus comprising:
means for generating a static magnetic field in a space where an object to be examined is accommodated, means for generating gradient magnetic fields to impart a gradient to the static magnetic field, a transmitting system for repeatedly applying radio frequency pulses according to a predetermined pulse sequence to cause nuclear magnetic resonance of nuclear spins of atoms constituting living tissue of the object, a receiving systems for detecting echo signals emitted by the nuclear magnetic resonance, a signal processing system for performing image reconstruction operation using the echo signals detected by the receiving system, means for displaying the obtained images, and a controlling system for controlling operations of the gradient magnetic field generating means, transmitting system, receiving system, and signal processing system, wherein a sequence for imaging a predetermined region by a plurality of slice acquisitions is performed repeatedly while changing an order of exciting a plurality of slices, echo signals obtained in the sequences are subjected to subtraction operation for corresponding slices, and the subtracted data are subjected to reconstruction operation to obtain images of the predetermined region.

4. Magnetic resonance angiography method for obtaining flow images by repeatedly performing an excitation by radio frequency magnetic field irradiation and acquisition of echo signals for a plurality of slice surfaces and reconstructing the flow images using the echo signals, comprising, a step (a) of performing a first measurement of exciting the plurality of slices in a first order and a second measurement of exciting the plurality of slices in an order opposite to the first order to obtain two kinds of data for each slice, and a step (b) of performing subtraction operation of the two kinds of data for each slice to obtain signals of flows in opposite directions as data with different signs.

5. Magnetic resonance angiography method of claim 4, wherein the step (a) further includes, prior to the first and second measurements, a step (c) of applying a radio frequency magnetic field to presaturate nuclear spins of a region adjacent to a slice to be excited first among the plurality of slices.

6. Magnetic resonance angiography method of claim 4, wherein each of the plurality of slices is selected to partially overlap another.

7. Magnetic resonance angiography method of claim 4, wherein two or more of echo signals phase encoded differently are acquired every excitation for each slice in the first and second measurements.

8. Magnetic resonance angiography method of claim 4, further comprising, after the step (b), a step (d) of selecting data having an absolute value of a threshold value or greater from the data with different signs, a step (e) of performing projection of the selected data to form projected flow images, and a step (f) of imparting color of different hue or different brightness to the flow images depending on the sign and displaying the flow images.

9. Magnetic resonance angiography method of claim 4, wherein data of slices positioned at the both sides of the region are deleted from data of the plurality of slices.

10. A magnetic resonance imaging apparatus comprising a magnet for generating a static magnetic field in a space where an object to be examined is accommodated, a radio frequency coil(s) for applying a radio frequency pulse and for detecting echo signals generated by the application of a radio frequency pulse, a CPU for performing an image reconstruction operation using the echo signals, a display for displaying the reconstructed images, and a sequencer for controlling applications of static magnetic field, gradient magnetic field, and radio frequency pulses according to a predetermined sequence, wherein the sequencer performs
a first measurement of detecting echo signals of flow for individual slices which comprises performing a sequence of detecting one or plural echo signals by applying radio frequency pulses to individual slices while selecting the positions of the slices for imaging a predetermined region, and controlling the application of the radio frequency pulses to apply the pulses at desired time intervals, and a second measurement of detecting echo signals of flow by performing a sequence similar to that of the first measurement while selecting the positions of slices in a manner opposite to the first measurement, and the CUP performs
subtraction operation of data or images of corresponding slices obtained by the first measurement and the second measurement.

11. The magnetic resonance imaging apparatus of claim 10, wherein the sequencer effects control to select the positions of slices so that adjacent slices overlap.

12. The magnetic resonance imaging apparatus of claim 10, wherein the CPU effects control to perform image reconstruction operation of two dimension or three dimension projection images using subtracted images or data of the individual slices.

* * * * *